(12) United States Patent
Matsumoto

(10) Patent No.: US 8,244,010 B2
(45) Date of Patent: Aug. 14, 2012

(54) IMAGE PROCESSING DEVICE AND A CONTROL METHOD AND CONTROL PROGRAM THEREOF

(76) Inventor: Kazuhiko Matsumoto, Tokyo (JP)

(*) Notice: Subject to any disclaimer, the term of this patent is extended or adjusted under 35 U.S.C. 154(b) by 821 days.

(21) Appl. No.: 12/271,118

(22) Filed: Nov. 14, 2008

(65) Prior Publication Data
US 2009/0129642 A1   May 21, 2009

(30) Foreign Application Priority Data
Nov. 21, 2007   (JP) ................ 2007-301947

(51) Int. Cl.
*G06K 9/00*   (2006.01)
(52) U.S. Cl. ........................ 382/128
(58) Field of Classification Search ........ 378/4, 19, 378/62; 382/128, 130–132
See application file for complete search history.

(56) References Cited

U.S. PATENT DOCUMENTS

| | | | | |
|---|---|---|---|---|
| 2007/0223807 A1* | 9/2007 | Yankelevitz et al. | ......... | 382/159 |
| 2009/0016579 A1* | 1/2009 | White et al. | ......... | 382/128 |
| 2011/0142301 A1* | 6/2011 | Boroczky et al. | ......... | 382/128 |

FOREIGN PATENT DOCUMENTS

| | | |
|---|---|---|
| JP | 2005-110974 | 4/2005 |
| JP | 2007-037781 | 2/2007 |
| JP | 2007-094513 | 4/2007 |

* cited by examiner

*Primary Examiner* — Irakli Kiknadze
(74) *Attorney, Agent, or Firm* — Fish & Associates, PC

(57) ABSTRACT

An image processing device that quickly performs suitable image processing by using an input device to point at an image displayed on the medical image processing device, and makes it possible to readily observe medical images needed for a medical procedure. The medical image processing device includes: an input element by which medical information that includes at least patient information, and the image processing type that uses the medical image data is input; an extraction element for extracting combinations of the medical image data that conform to the patient information and the image processing type; an evaluating unit for evaluating out combinations of medical image data that have the highest possibility of being used; an information reporting unit for reporting of the combinations of medical image data and evaluating result information; and a selection unit for prompting a user to select the combination of medical image data.

30 Claims, 7 Drawing Sheets

FIG. 5

| ATTRIBUTE INFORMATION | CONTENT SUMMARY |
|---|---|
| PATIENT INFORMATION | PATIENT'S NAME |
| IMAGING DEVICE INFORMATION | IMAGE PROCESSING DIFFERS DEPENDING ON THE DEVICE USED |
| IMAGING DATE INFORMATION | DATE IMAGES WERE TAKEN |
| IMAGING TIME INFORMATION | JUDGMENT OF WHETHER OR NOT IMAGE DATA IS TIME SEQUENCE DATA |
| IMAGING CONDITION INFORMATION | IMAGING CONDITIONS UNIQUE TO THE IMAGE PROCESSING |
| IMAGING COORDINATE INFORMATION | SPECIFICATION OF ORGANS OR THE LIKE WHOSE IMAGE IS TAKEN |
| IMAGING SCALE INFORMATION | SCALE DIFFERENCES |
| CONTRAST AGENT USAGE INFORMATION | IMAGE PROCESSING FOR WHICH A CONTRAST AGENT IS NECESSARY |

FIG. 7A

| CT IMAGES | VOLUME DATA A | RANGE |
| | VOLUME DATA B | 100 ... 300 |
| MRI IMAGES | VOLUME DATA C | RANGE |
| | VOLUME DATA D | 0 ... 50 |

FIG. 7B

| MRI IMAGES | MOVING IMAGE DATA A | RANGE |
| | MOVING IMAGE DATA B | 0 ... 45 |
| | MOVING IMAGE DATA C | |
| | MOVING IMAGE DATA D | |

IMAGE PROCESSING DEVICE AND A CONTROL METHOD AND CONTROL PROGRAM THEREOF

BACKGROUND OF THE INVENTION

1. Field of the Invention

This invention relates to an image-processing device that provides medical image data that correspond to the type of image processing, and to an image processing method and image processing program thereof

2. Description of the Related Art

With the advancement and development of image processing technology that uses computers, CT (Computed Tomography), MRI (Magnetic Resonance Imaging), PET (Position Emission Tomography) and the like, which make it possible to directly observe the internal tissue of the human body, have emerged, and technologies such as these have brought about innovation in the medical field, so that currently medical diagnosis that uses tomographic images (slice data) of the body is widely being performed. In medical diagnosis, not only is technology being used in which it is possible to display slice data, but technology, such as volume rendering that directly draws images of 3-dimensional tissues from 3-dimensional digital data (volume data) of the body that are obtained from CT, is also being used that makes it possible to visualize complicated 3-dimensional tissues inside the human body that are difficult to comprehend with just tomographic images. Moreover, in volume rendering, the Raycast method, the MIP (Maximum Intensity Projection) method, the MPR (Multi Planar Reconstruction) method that cuts out arbitrary cross sections from the volume data and displays those cross sections, and the CPR (Curved Multi Planer Reconstruction) method are typically used for the 3-dimensional image processing in volume rendering. Furthermore, the medical image data are stored in a memory device.

ID information such as normal Study ID and Series ID information are attached to the medical image data.

Study ID (Identification) information is attribute information that expresses the logical unit of slice data that can be set arbitrarily in accordance to circumstances on the imaging side. Generally, this is a image data group that are necessary for one diagnosis, which may includes one or more volume data, some rendered image and diagnostic result. For example, in the case that cancer is suspect, this may be slice data groups for one or a plurality of imaging devices from one or more days for identifying whether or not there is cancer and/or the size of the cancer The same Study ID information is included in all of the slice data of the slice data group.

Series ID information is attribute information for identifying one or more slice data for one imaging device when an imaging is requested (the same Series ID information is included in all of the slice data). For example, one volume of data may be constructed by combining items of medical image data that contain the same Series ID.

Medical image data process that use this medical image data include types of image processing such as graphic processing that uses 4-dimensional data, CT-PET fusion processing that simultaneously displays CT images and PET images, display processing of 2-dimensional moving images (e.g. moving images by angiography), MR brain perfusion processing, coronary artery analysis, and the like. In order to execute these processes, the doctor or radiologist, who is the user, specifies combinations of medical image data that are considered to be most appropriate for each process from the memory device where it is stored together with other medical image data, and specifies a combination of medical image data while viewing all or part of the medical image data and the attributes thereof, then executes each process to create each of the various images.

The combinations of medical image data that are necessary for executing each of the various aforementioned processes differ according to the contents of the process, so suitable combinations must be selected from among a plurality of medical image data, and in order to execute a desired process, it is necessary to search for a suitable combination of medical image data, and then select and specify the desired medical image data. This work poses problems for the doctor or radiologist, who is the user, in that the operations are troublesome and require much time, which is stressful for the user, and there is a possibility that the work will interfere with proper medical practice.

Therefore, conventionally, the imaging device attached Study ID and Series ID information to the medical image data, however, the imaging device did not have the information for each of the processes described above, so the most suitable ID information was not always attached. For example, even though imaging is performed for the entire body as the object, analysis may be performed for just a certain organ as the object. Also, in the case of obtaining medical image data from a plurality of devices and combining that data for use, each imaging device attached totally unrelated ID information, so it was not possible to obtain a suitable combination of medical image data from just the ID information.

Moreover, when a wrong combination of medical image data is specified, the program that executes the processing will reject input of that wrong combination of medical image data, or an erroneous image will be displayed, so there was a problem in that the operation for specifying a combination of medical image data was difficult.

Furthermore, since the amount of medical image data is normally very large, much time was required from the time the user specified the medical image data until the image processing was executed, so there was a problem in that useless waiting time occurred.

SUMMARY OF THE INVENTION

Taking into consideration the problems described above, the object of the present invention is to provide an image processing device and a control method and control program thereof that quickly perform suitable image processing by performing operation using an input device such as a pointing device to point at an image that is displayed on the medical image processing device, which makes it possible to readily observe medical images needed for a medical procedure The present invention recited in Claim 1 for solving the problems is directed to a medical image processing device that uses medical image data that contain attribute information, that is provided with: an input means for inputting medical information that includes at least patient information, and an image processing type that uses the medical image data; an extraction means for using at least the attribute information to extract combinations of the medical image data that conform to the patient information and the image processing type; an evaluating means for evaluating out combinations of medical image data from the combinations of medical image data extracted by the extraction means that have the highest possibility of being used in image processing of the image processing type; an information reporting means for reporting of the combinations of medical image data and evaluating result information, which is the result of evaluating by the evaluating means; and a selection means for prompting a user to select the combination of medical image data that was reported by the information reporting means.

With this invention, combinations of medical image data, which are suitable candidates that conform to the image processing desired by the user, can be presented to the user from among an enormous amount of medical image data.

Moreover, the user can select a suitable combination of medical image data that conforms to the desired image processing, so it is possible to prevent the user from selecting the wrong combination of medical image data, and the selection operation by the user itself is simplified.

Furthermore, in the case where the user must observe a plurality of medical image data (series) for the same patient one after the other, redundant operation by the user has been done away with, so it is possible for the user to perform the selection operation quickly and easily.

In addition, combinations of medical image data having the highest priority among the candidates are presented to the user, so when a presented combination of medical image data coincides with the selection of combination of medical image data by the user, operation by the user is simplified by increasing the speed of image processing and doing away with operation related to explicit selection.

Moreover, the image processing device automatically performs the extraction and evaluating (arranging the order of priority) of combinations of medical image data, so for a user that must process a large amount of images for medical use in a single day, it is possible to do away with the complicated operation of extracting and evaluating combinations of medical image data, and thus it is possible to lighten the burden on the user and to greatly reduce judgmental and operational errors.

The present invention recited in Claim 2 for solving the problems is directed to the medical image-processing device of claim 1, wherein there are drawing settings (including rendering parameter, WW/WL, color look up table for raycast method and opacity look up table for raycast method) that correspond to the type of image processing; and after the selection means selects the combination of medical image data, the medical image data are drawn according to the drawing settings.

With this invention, when performing image processing using a combination of medical image data that was selected by the user, drawing settings are performed that correspond to the method used for visualizing the medical image data that is recommended for the respective types of image processing, so it is possible to eliminate the time required for the user to reset the drawing settings, and since uniform and standardized drawing can be performed, more accurate analysis can be expected.

The present invention recited in Claim 3 for solving the problems is directed to the medical image-processing device of claim 1, wherein the combinations of medical image data form at least volume data.

With this invention, the image-processing device can provide the user with volume data that comprises a plurality of slice data in a 3-dimensional array as a combination of medical image data. Therefore, the image-processing device can create a set of image data for routined unit of diagnosis having with a high degree of freedom and having few restraints on the logical format, and thus is able to provide medical image data or a combination of medical image data in routined diagnosis easy for the user to handle.

Moreover, the routined unit of diagnosis of the medical image data is a unit that fits the senses of the user, so display screens are easy to view and it becomes possible to perform suitable judgment for image processing. Furthermore, it is possible to lighten the burden on the user and to greatly reduce judgmental and operational errors.

The present invention recited in Claim 4 for solving the problems is directed to the medical image-processing device of claim 1, wherein when the image processing type is fusion processing information, the extraction means extracts at least two combinations of medical image data of the region around the same site of the patient.

With the present invention, when the input image processing type is fusion processing, it is known in advance that the image processing is image processing that uses at least two or more combinations of medical image data for the region around the same site, so by searching for medical image data for the same site, the work of searching for medical image data that is suitable for image processing from among an enormous amount of medical image data is simplified.

Moreover, the amount of operation by the user is reduced, and no unnecessary burden and labor is placed on the user (the design becomes user friendly).

The present invention recited in Claim 5 for solving the problems is directed to the medical image-processing device of claim 1, wherein the patient information is included in the attribute information of the medical image data, and furthermore, at least one or more of imaging device information, imaging date information, imaging time information, imaging condition information, imaging coordinate information, imaging scale information, and information of whether or not a contrast agent is used are included as attribute information.

With this invention, various information is included in the medical image data, so when the user executes the desired image processing, the image processing device is able to quickly extract combinations of medical image data that conform to the image processing desired by the user from a large amount of medical image data.

Also, since there is no repeated burden on the user to frequently operate the user interface to search for medical image data, it is possible to provide the user with an image-processing device having good operability.

The present invention recited in Claim 6 for solving the problems is directed to the medical image processing device of claim 1, that is further provided with an acquisition means for acquiring beforehand the combinations of medical image data that were evaluated out by the evaluating means before a user uses the selection means to select the combination of medical image data.

With the present invention, construction is such that combinations of medical image data that are best candidates having the highest priority are provided to the user, so when evaluating by the image processing device (prioritizing combinations of medical image data) coincides with the selection of a combination of medical image data by the user, it is possible to speed up the image processing.

Moreover, the image processing device automatically extracts and evaluates (prioritizes) combinations of medical image data, and without waiting to obtain medical image data having a slow transfer speed, stores combinations of medical image data having high priority onto a high-speed memory medium inside the image processing device before the user performs any operation, so a high-speed image processing device that can immediately execute image processing with little wait time by the user is possible.

The present invention recited in Claim 7 for solving the problems is directed to the medical image-processing device of claim 1, wherein conditions that were used when the extraction means extracted the combination of medical image data that was selected by the selection means and the patient information, are used in extracting a new combination of medical image data that conforms to the type of image processing With this invention, there may be cases in which there are combinations of medical image data for each imaging period when observing the progression over time of a certain patient for example. In that case, observation is performed using combinations of medical image data that include the most recent progression over time, and when for comparison it is desired to observe past progression over time using the similar form, by processing suitable combinations of medical image data that include past progressions over time, it is possible to perform the objective examination more quickly.

The present invention recited in Claim 8 for solving the problems is directed to the medical image-processing device of claim 1, conditions that were previously used when the extraction means extracted the combination of medical image data that was selected by the selection means and the patient information of an another patient of the patient of the patient information is stored, are used in extracting a new combination of medical image data that conforms to the type of image processing.

With the present invention, there may be cases, such as in a screening examination, where the same examination is performed in succession for different patients. In that case, it is convenient to perform image processing in succession using the same conditions for the different patients. With this invention, the user is presented with combinations of medical image data having the same conditions, so it is possible to perform examination more quickly and with objectivity.

The present invention recited in Claim 9 for solving the problems is directed to the medical image-processing device of claim 1, wherein the extraction means uses the combination of medical image data that was selected in the past by the selection means based on an image processing type, which is the same as the image processing type that was input by the input means, to extract a new combination of medical image data.

With the present invention, when the image processing device stores combinations of medical image data that were selected before by the user as log information, and the same image processing is input by the user, the image processing device searches for combinations of medical image data based on that log information (learning function), so a faster and more efficient image processing device becomes possible.

The present invention recited in Claim 10 for solving the problems is directed to the medical image-processing device of claim 1, wherein the medical image data are acquired from a medical image data storage means.

With this invention, the image processing device can be used as a client server type image processing device instead of as a stand-alone type of device, so by storing medical image data in an external database, the medical image database can be easily maintained, and it becomes possible for many users to use (share) medical image data from a terminal device.

The present invention recited in Claim 11 for solving the problems is directed to a control method for controlling a medical image processing device that uses medical image data that contains attribute information, comprising: an input process of inputting medical information that includes at least patient information, and an image processing type that uses the medical image data; an extraction process of using at least the attribute information to extract combinations of the medical image data that conform to the patient information and the image processing type; a evaluating process of evaluating out combinations of medical image data from the combinations of medical image data extracted in the extraction process that have the highest possibility of being used in image processing of the image processing type; an information reporting process of reporting of the combinations of medical image data and evaluating result information, which is the result of evaluating in the evaluating process; and a selection process of prompting a user to select the combination of medical image data that was reported in the information reporting process.

The present invention recited in Claim 12 for solving the problems is directed to the method of controlling a medical image-processing device of claim 11, wherein there are drawing settings that correspond to the type of image processing; and after the selection means selects the combination of medical image data, the medical image data are drawn according to the drawing settings.

The present invention recited in Claim 13 for solving the problems is directed to the method of controlling a medical image-processing device of claim 11, wherein the combinations of medical image data form at least volume data.

The present invention recited in Claim 14 for solving the problems is directed to the method of controlling a medical image-processing device of claim 11, wherein when the image processing type is fusion processing information, at least two combinations of medical image data of the region around the same site of the patient are extracted in the extraction process.

The present invention recited in Claim 15 for solving the problems is directed to the method of controlling a medical image-processing device of claim 11, wherein the patient information is included in the attribute information of the medical image data, and furthermore, at least one or more of imaging device information, imaging date information, imaging time information, imaging condition information, imaging coordinate information, imaging scale information, and information of whether or not a contrast agent is used are included as attribute information.

The present invention recited in Claim 16 for solving the problems is directed to the method of controlling a medical image processing device of claim 11, that is further provided with an acquisition process of acquiring beforehand the combinations of medical image data that were evaluated out in the evaluating process before a user selects the combination of medical image data in the selection process.

The present invention recited in Claim 17 for solving the problems is directed to the method of controlling a medical image-processing device of claim 11, wherein the conditions that were used in the extraction process when extracting the combination of medical image data that was selected by the selection means and the patient information, are used in extracting a new combination of medical image data that conforms to the type of image processing.

The present invention recited in Claim 18 for solving the problems is directed to the method of controlling a medical image-processing device of claim 11, wherein the conditions that were used in the extraction process when extracting the combination of medical image data that was selected by the selection means and patient information of an another patient of the patient of the patient information is stored, are used in extracting a new combination of medical image data that conforms to the type of image processing.

The present invention recited in Claim 19 for solving the problems is directed to the method of controlling a medical image-processing device of claim 11, wherein the extraction process uses the combination of medical image data that was selected in the past in the selection process based on an image processing type, which is the same as the image processing type that was input in the input process, to extract a new combination of medical image data.

The present invention recited in Claim 20 for solving the problems is directed to the method of controlling a medical image-processing device of claim 11, wherein the medical image data are acquired from a medical image data storage process.

The present invention recited in Claim 21 for solving the problems is directed to a control program for a medical image-processing device that causes a computer that is included in the medical image-processing device, which uses medical image data that contain attribute information, to function as: an input means for inputting medical information that includes at least patient information, and an image processing type that uses the medical image data; an extraction means for using at least the attribute information to extract combinations of the medical image data that conform to the patient information and the image processing type; an evaluating means for evaluating out combinations of medical image data from the combinations of medical image data extracted by the extraction means that have the highest possibility of being used in image processing of the image processing type; an information reporting means for reporting of the combinations of medical image data and evaluating result information, which is the result of evaluating by the evaluating means; and a selection means for prompting a user to select the combination of medical image data that was reported by the information reporting means.

The present invention recited in Claim 22 for solving the problems is directed to the control program for a medical image-processing device of claim 21, wherein there are drawing settings that correspond to the type of image processing; and after the selection means selects the combination of medical image data, the medical image data are drawn according to the drawing settings.

The present invention recited in Claim 23 for solving the problems is directed to the control program for a medical image-processing device of claim 21, wherein the combinations of medical image data form at least volume data.

The present invention recited in Claim 24 for solving the problems is directed to the control program for a medical image-processing device of claim 21, wherein when the image processing type is fusion processing information, the extraction means extracts at least two combinations of medical image data of the region around the same site of the patient.

The present invention recited in Claim 25 for solving the problems is directed to the control program for a medical image-processing device of claim 21, wherein the patient information is included in the attribute information of the medical image data, and furthermore, at least one or more of imaging device information, imaging date information, imaging time information, imaging condition information, imaging coordinate information, imaging scale information, and information of whether or not a contrast agent is used are included as attribute information.

The present invention recited in Claim 26 for solving the problems is directed to the control program for a medical image processing device of claim 21, that is further provided with an acquisition means for acquiring beforehand the combinations of medical image data that were evaluated out by the evaluating means before a user uses the selection means to select the combination of medical image data.

The present invention recited in Claim 27 for solving the problems is directed to the control program for a medical image-processing device of claim 21, wherein the conditions that were used when the extraction means extracted the combination of medical image data that was selected by the selection means and the patient information, are used in extracting a new combination of medical image data that conforms to the type of image processing.

The present invention recited in Claim 28 for solving the problems is directed to the control program for a medical image-processing device of claim 21, wherein the conditions that were used when the extraction means extracted the combination of medical image data that was selected by the selection means and patient information of an another patient of the patient of the patient information is stored, are used in extracting a new combination of medical image data that conforms to the type of image processing.

The present invention recited in Claim 29 for solving the problems is directed to the control program for a medical image-processing device of claim 21, wherein the extraction means uses the combination of medical image data that was selected in the past by the selection means based on an image processing type, which is the same as the image processing type that was input by the input means, to extract a new combination of medical image data.

The present invention recited in Claim 30 for solving the problems is directed to the control program for a medical image-processing device of claim 21, wherein the medical image data is acquired from a medical image data storage means.

BRIEF DESCRIPTION OF THE DRAWINGS

FIG. 5 is a drawing that explains attribute information for the medical image data.

FIGS. 7A and 7B are drawings that explain the image selected according to the image processing.

DETAILED DESCRIPTION OF THE PREFERRED EMBODIMENTS

The preferred embodiments of the invention are explained based on the supplied drawings.

[1. Example of the System Configuration]

Figure 1B:
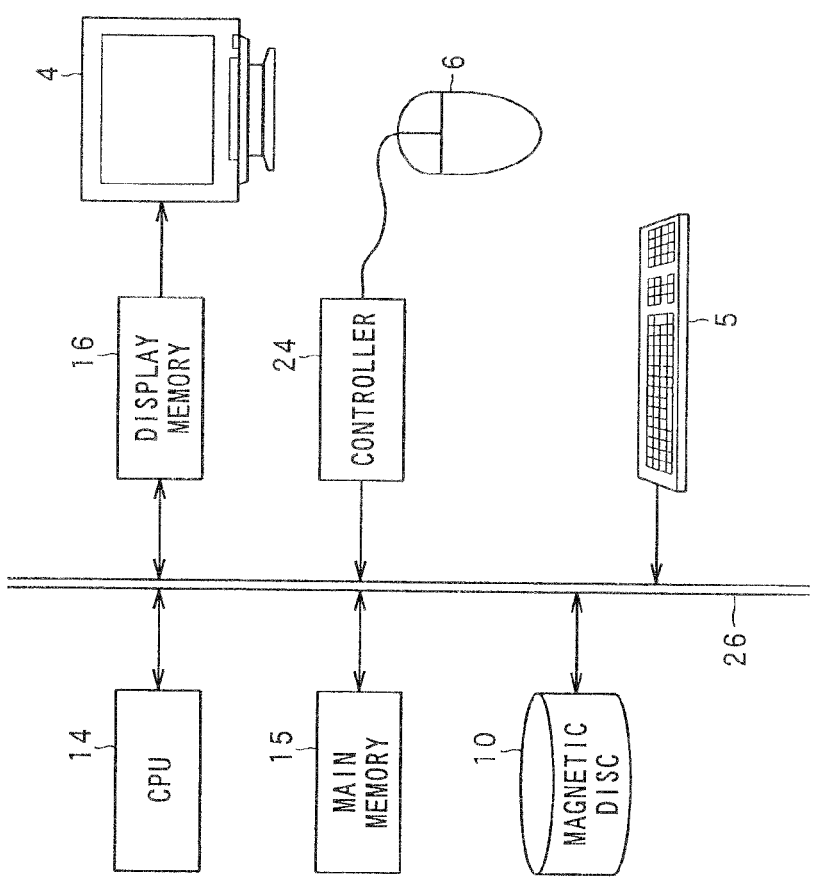
FIG. 1B is a drawing showing an example of the hardware configuration of an embodiment of the invention.
Figure 1A:
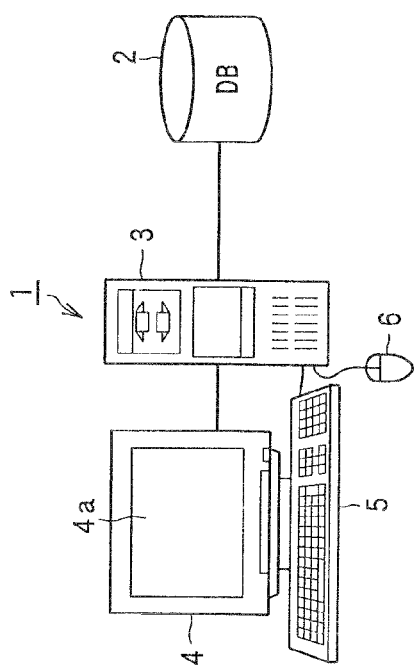
FIG. 1A is a drawing showing an example of the system configuration of an embodiment of the invention.

FIGS. 1A is a block diagram showing an example of the system configuration of the invention (an embodiment of the invention).

As shown in FIG. 1A, an image display device 1 reads CT image data that were acquired by a CT imaging device, then creates various images for medical analysis and displays those images on a screen. In this case, an example of using CT image data is explained, however, this embodiment is not limited to CT image data. In other words, the medical image data to be used is not limited to CT image data, and can include medical image data that is obtained from a medical image processing device such as MRI, PET and the like, or other further processed medical image data.

The image display device 1 comprises: a computing device (computer, work station, personal computer or the like) 3, a monitor 4, and an input device such as a keyboard 5 and mouse 6 as examples of an input means and selection means. The computing device 3 is connected to a database 2 as a medical image storage device.

FIG. 1B is a block diagram that shows an example of the hardware configuration of the image display device 1 that uses the method of the present invention. As shown in FIG. 1B, this image display device 1 comprises: a magnetic disc 10, a main memory 15 as an acquisition means; a central processing unit (CPU) 14 as an extraction and evaluating means; a display memory 16; a monitor 4 as an example of an information notification means, a keyboard 5 as another example of an input and selection means; a mouse 6 as a pointing device for inputting various operation instructions, position instructions and menu selection instructions; a mouse controller 24; and a common bus 26 that connects each of these components. In addition, it is also possible to have a sound output means drive unit for driving a sound output means such as a speaker (not shown in the figure), or a display means drive unit for driving a display means such as a monitor 4 (not shown in the figure).

A plurality of tomographic images, an image creation program and the like are stored on the magnetic disc 10, and as necessary, tomographic images (medical image data) are read from an external database 2 that is connected to the common bus 26 and stored on the magnetic disc 10. The control program for the device and medical image data for image processing are stored in the main memory 15, as well as an area for computational processing is prepared in the main memory 15. The CPU 14 reads a plurality of tomographic images and various programs (including the image processing program), and uses the main memory 15 to create pseudo 3-dimensional images and expanded cross-sectional images, then sends the image data for displaying those created images to the display memory 16 and displays the images on the monitor 4.

Figure 2:
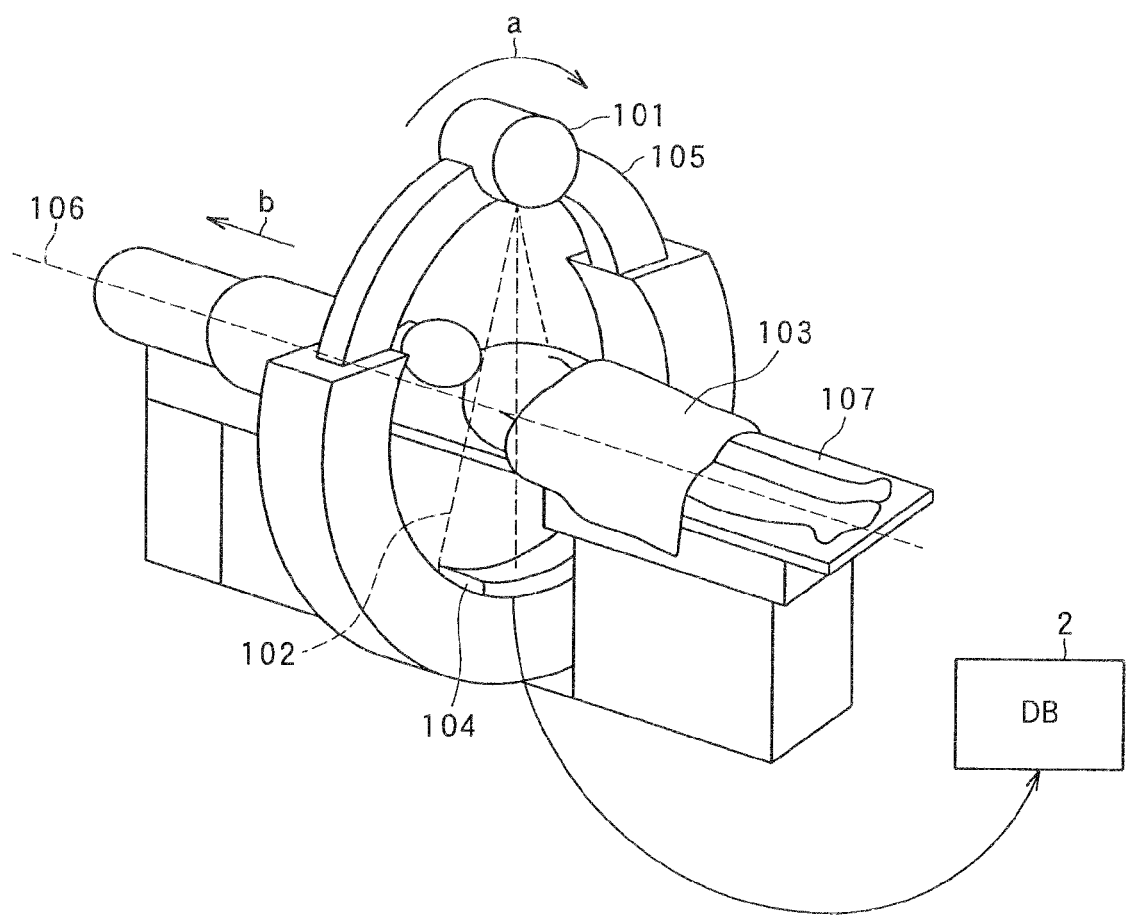
FIG. 2 is a drawing showing an example of the imaging system of an embodiment of the invention.

Next, FIG. 2 will be used to explain the data that are stored in the database 2. FIG. 2 shows a computed tomography imaging (CT) device that is used in the image processing method of a first embodiment of the invention. The computed tomography imaging device makes it possible to visualize the tissue of the body being examined (site). A pyramid shaped X-ray beam bundle 102 having a marginal beam as shown by the dashed line in FIG. 2 is emitted from an X-ray source 101. The X-ray beam bundle 102 passes through the body of the patient 103 that is being examined and is irradiated onto an X-ray detector 104. In this embodiment of the invention, the X-ray source 101 and X-ray detector 104 are located in a ring-shaped gantry 105 so that they face each other. The ring-shaped gantry 105 is supported by a support device (not shown in the figure) so that it can rotate (see arrow a) around the system axis line 106, which passes through the center point of the gantry.

In this embodiment of the invention, the patient 103 lies on a table 107 through which the X-rays pass. This table is supported by a support device (not shown in the figure) so that it can move along the system axis line 106 (see arrow b).

Therefore, a measurement system is formed in which the X-ray source 101 and X-ray detector 104 can rotate around the system axis line 106, and can move along the system axis line 106 relative to the patient 103, so images of the patient 103 can be taken from various angles and various positions with respect to the system axis line 106. When doing this, the output signal that is generated by the X-ray detector 104 is supplied to a volume data generation unit 111 and converted to volume data.

In the case of sequence scanning, each tomographic layer of the patient 103 is scanned. When doing this, the X-ray source 101 and X-ray detector 104 rotate around the patient 103 with the system axis line 106 as the center of rotation, and the measurement system, which includes the X-ray source and X-ray detector 104, takes a plurality of images for scanning 2-dimensional layers of the patient 103. At this time, a tomographic image that shows the scanned layers is reconstructed from the acquired measurement values. The patient 103 is moved along the system axis line 106 while scanning the phase continuous layers. This process is repeated until all of the layers of interest have been acquired.

On the other hand, during spiral scanning, the measurement system, which includes the X-ray source 101 and the X-ray detector 104, rotates with the system axis line 106 as the center of rotation, and the table 107 continuously moves in the direction of arrow b. That is, the measurement system, which includes the X-ray source 101 and the X-ray detector 104, moves continuously over a spiral track relative to the patient 103 until all of the areas of interest of the patient 103 have been acquired. In the case of this embodiment, using the computed tomography imaging device that is shown in FIG. 2, a plurality of relative and continuous tomographic layer signals for the diagnosis range of the patient 103 is stored in the database 2.

[2. Explanation of Volume Data]

The minimum unit of medical image data is one image, and each tomographic image (acquired from a computer tomographic image device such as a CT device) is called slice data. This slice data has a format such as DICOM (Digital Imaging and Communication in Medicine) format that sets the communication conditions and the attribute information for the slice data.

Figure 3:
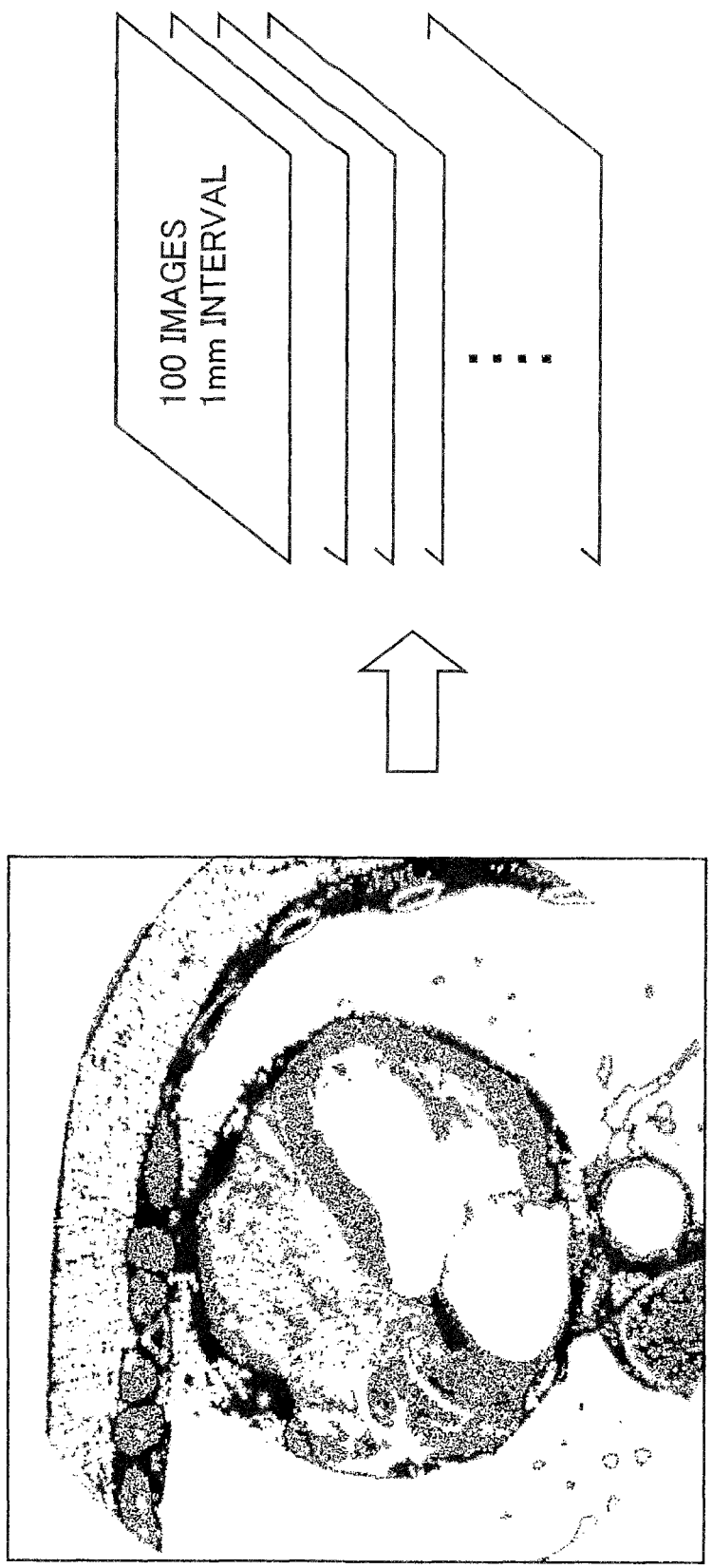
FIG. 3 is a drawing that explains the medical image data.

Next, volume data, which is a combination of 3-dimensional or greater medical image data, will be explained. As shown in FIG. 3, slice data such as CT images are images taken of tomographic layers of the body of a patient, and each image is a 2-dimensional tomographic image of an observed bone, blood vessel or organ (may also be referred to as a site, or tissue) (see the left side of FIG. 3). The slice data are obtained from a plurality of adjacent cross sections (see the right side of FIG. 3), and can form a 3-dimensional array of image data that is expressed by all of the slice data. This 3-dimensional array of image data is called volume data. The volume data that are shown by the collection of slice data shown on the right side of FIG. 3 is expressed based on a plurality of slice data, comprising 100 images of space that includes part of the body and that are stacked at intervals of 1 mm.

More specifically, a collection of 3-dimensionally layered slice data is called volume data, and each of the 3-dimensional picture elements of that 3-dimensional array is called a Voxel. The 3-dimensional grid point of each voxel is assigned a density value as its voxel value. In this embodiment, a pixel of slice data such as CT image data, or in other words, the CT value itself, is taken to be the density value of the voxel data VD. Also, similarly, it is possible to take the value of MRI and PET image data itself to be the density value of Voxel data. In medical images, voxels are often represented by scalar values (monochrome) having the value −2048 to 2047. Normally, volume data comprises medical image data having the same ID information.

Moreover, CT image data has CT values that differ for each tissue of the body that is examined (for example, bone, blood vessel, organ). The CT value is the X-ray linear attenuation coefficient of the tissue that is expressed with water as a reference, and is such that it is possible to determine the type of tissue or lesion from the CT value. In addition, all CT image data also includes coordinate data for the tomographic layer data (slice data) of the body undergoing a CT scan by the CT imaging device, and physical coordinates on the body at a point on the slice data can be obtained from logical coordinates of an array that forms that slice data. Therefore, the positional relationship between tissues can be determined. That is, the voxel data VD comprises CT values (hereafter referred to as the voxel value) and coordinate data values.

Furthermore, volume data does not necessarily always have to use all slice data included in a series, and it is possible to freely combine medical image data. For example, when the resolution of an image required for analysis is low, it is possible to form volume data by skipping part of the slice data. Also, instead of performing imaging for the entire body, it is possible to form volume data for the area of just the part necessary for analysis. By doing so, the amount of memory needed for the volume data can be reduced, and thus it becomes possible to speed up processing.

[3. Explanation of Moving Images]

Figure 4A:
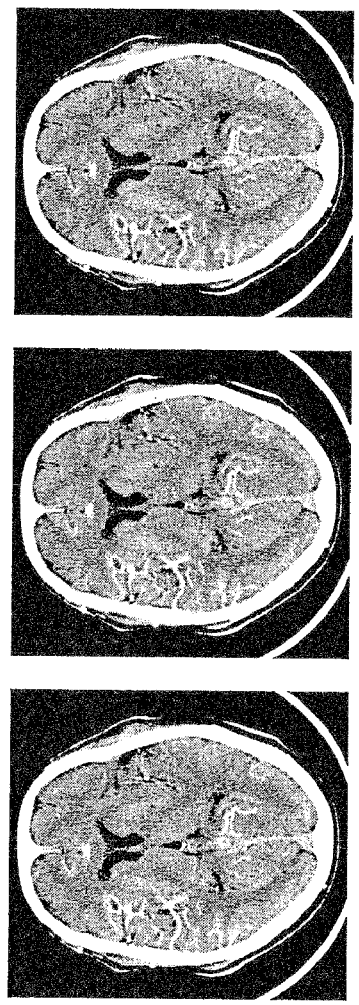
FIGS. 4A and 4B are drawings that explain moving images from medical image data.
Figure 4B:
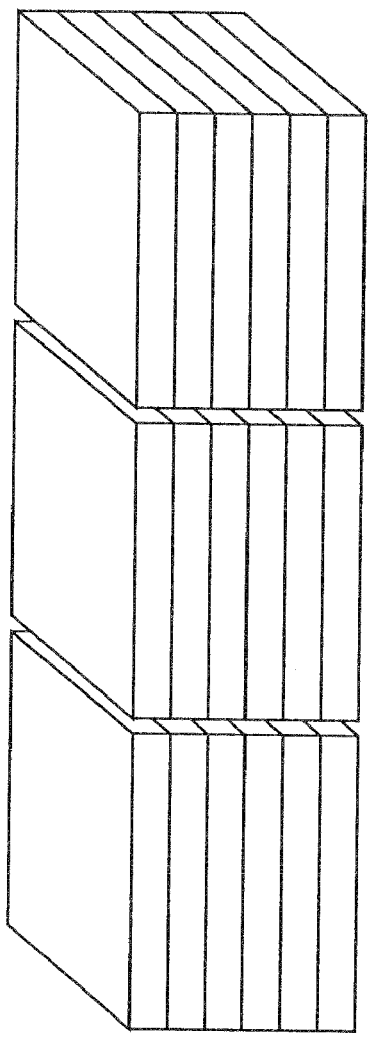

FIGS. 4A, 4B are drawings for explaining the combination of medical image data when expressing the medical image data as a moving image.

FIG. 4A is a drawing that explains the combination of medical image data when expressing 2-dimensional medical image data as a moving image, and FIG. 4B is a drawing that explains the combination of medical image data when expressing 3-dimensional medical image data as a moving image.

FIG. 4A shows the expression by a 2-dimensional moving image when slice data near the same portion is extracted several times in a time sequence (prepared as a combination of slice data), and slice data are continuously drawn on the monitor 4 in order of time (in order from the slice data taken at the latest time to the slice data taken at the earliest time, or in order from the slice data taken at the earliest time to the slice data taken at the latest time). This moving image is repeatedly displayed, and can be displayed in the order of time or reverse order of time. By doing this, it is possible for the user to observer the characteristic movement in a lesion.

Moreover, FIG. 4B shows the expression by a 3-dimensional moving image (3-dimensional image of part of the body such as an organ, blood vessel, etc.) when volume data near the same part is extracted a few times in a time sequence (prepared as a combination of volume data), and by continuously forming images on the monitor 4 of the target location in volume data (location (part or tissue of the body such as an organ, blood vessel, etc.) that the user specifies by specifying the correlation between the voxel value and opacity) in order of time (in order from the volume data taken at the latest time to the volume data taken at the earliest time, or in order from the volume data taken at the earliest time to the volume data taken at the latest time). Moreover, when there is not enough time to take an image of a beating organ such as the heart in one frame of one volume of data, volume data may be completed by taking images of one portion at a time in synchronization with the beating. In this case, volume data for a plurality of phases that form the beating is obtained, and it is possible to express a 3-dimensional moving image by successively displaying that plurality of volume data.

As was explained above, the medical image-processing device often handles the series of moving image data or volume data, which are a combination of medical image data, as one routined unit of diagnosis.

[5. Attribute Information of Medical Image Data]

FIG. 5 is a drawing that explains the information that is included in one slice of medical image data. The information that is included in medical image data can be classified into image information that expresses the image itself, ID information and other attribute information.

Image information is actual image data included in slice data, and is recorded in a preset format as a collection of black and white or color picture element data.

Patient information is the information for identifying the patient for which the image information is taken. The patient name can be input when the imaging device takes images for slice data, or can be input by an editing device after the images have been taken. Moreover, the format used can be arbitrarily set as long as the patient name can identify the patient for which the image information is taken. For example, the patient name can be expressed by ID labeling using the alphabet, katakana, hiragana, kanji, symbols, barcode (including 1-dimensional barcode and 2-dimensional barcode), graphics and the like (it is possible to express all of the kinds of information described below using the same kind of ID labeling).

The imaging device information is the attribute information for identifying the type of device that takes images for the slice data. The imaging device information includes ID labeling for classifying the type of imaging device such as a CT, MRI, PET or typical X-ray device, as well as includes model information for each type of imaging device (includes information that indicates devices that have undergone improvements or version upgrades), and production number information. The reason for including the model information and production number information of the imaging device is that there is a possibility that a different model of imaging device or a device for which the production number (lot number) has been changed may have different output results from the imaging device before the model change or the change in production number, and that could affect analysis.

Furthermore, the type of image processing used for processing the medical image data differs depending on the type of imaging device used, so imaging device information is necessary when the CPU 14 extracts and selects medical image data according to the type of image processing.

Imaging date information is the attribute information for identifying the date on which slice data was taken. For example, when the CPU 14 recognizes that the imaging date on which a plurality of slice data was taken for the same patient is the same, the CPU 14 is able to determine that there is a possibility that the slice data for which the imaging date is the same is the medical image data for the same location (for example, cancer examination, large intestine examination, brain examination, etc.).

Imaging time information is the attribute information for identifying the time when slice data images were taken When the slice data is to be used as moving image data, the CPU 14 determines the time before and after based on imaging time information, and that information is used when determining whether or not to extract and evaluate the slice data as a series of processing data. Also, even in the case of one image of slice data, this information is used when the CPU 14 determines whether to extract and select the most recent slice data, or to whether to extract and evaluate the oldest slice data.

Imaging condition information is the attribute information for identifying the imaging conditions under which the slice data images are taken. Of the types of image processing there is image processing that uses only medical image data taken under special imaging conditions. For example, this information includes imaging direction (angle) information of the area for which the image is to be taken and filter processing applied by the imaging device on the image. Therefore, when the imaging conditions are included in the slice data as information, the CPU 14 is able to easily extract and evaluate slice data that are medical image data that corresponds to the input imaging processing.

Imaging coordinate information is the information for identifying imaging coordinates of the slice data images that are taken. Imaging coordinate information is expressed by absolute coordinate values or relative coordinate values from arbitrary physical coordinates of the imaging device. Moreover, the CPU 14 references the imaging device information as one kind of information for recognizing how the imaging coordinate information is set (information such as the coordinate reference point, method of indicating the coordinate axes, absolute or relative coordinate values).

In this way, the CPU 14 is able to recognize from the imaging coordinate information which area around a site (organ or tissue of the body) of the patient the slice data belong to. When items of slice data are from around the same site, by referencing other information, the CPU 14 is able to extract and evaluate the slice data as one routined unit of diagnosis for moving image data. Moreover, in the case of volume data that includes overlapping regions, it becomes possible to treat the volume data as one routined unit of diagnosis for drawing 3-dimensional moving images, and treat at least two or more volume data as one routined unit of diagnosis.

Imaging scale information (pixel spacing) is attribute information for identifying how much the size of the slice data of the site on the patient where imaging is performed has been enlarged or reduced from the actual size. When the image-processing device executes image processing, it is necessary for the image-processing device to handle medical image data having the same scale by extracting and evaluating slice data that have the same scale, or by converting slice data having different scales to the same scale. Therefore, the imaging scale information includes enlargement percentage information or reduction percentage information that indicates how much the data are to be enlarged or reduced.

Contrast agent usage information is the attribute information that indicates whether or not contrast agent was used when taking the slice data images. For example, only slice data that use a contrast agent is used in imaging data that is taken using angiography (blood vessel examination), and image processing such as MR brain perfusion processing and coronary artery analysis processing, so when the user inputs the type of image processing such as display processing of imaging data by angiography (blood vessel examination), MR brain perfusion processing, or coronary artery analysis processing, the CPU 14 extracts just slice data images that were taken using a contrast agent according to the contrast agent usage information.

The various kinds of information for the medical image data were explained above, however, the present invention is not limited to the kinds of information for the medical image data described above, and various kinds of information for identifying the slice data or groups of slice data that are used in the image processing that will be described later are included in the medical image data.

[6. Types of Image Processing]

The types of image processing will be explained next.

The types of image processing are normally divided into general image processing and special image processing.

General image processing is processing such as general volume analysis processing, 4-dimensional volume analysis processing, CT-PET fusion processing, display processing of 2-dimensional moving images that are obtained using angiography (blood vessel examination), and special image processing is image processing such as MR brain perfusion processing arid coronary artery analysis processing.

First, general image processing will be explained

As described above, general volume analysis processing is image processing that draws volume data that comprises a plurality of discretely continuous slice data (space that is expressed as a 3-dimensional array) as 3-dimensional medical images from an arbitrary angle using a rendering method When general volume analysis processing is executed, the user can observe a still image on the monitor 4 of a specified site or tissue of the body that is specified from the coordinates of the slice data. In this processing (general volume analysis processing), a plurality of slice data that is mainly from CT processing is often extracted by the CPU 14 as a combination of medical image data that is suitable for general volume analysis processing.

4-dimensional volume analysis processing is image processing that, even though there is volume data that comprises a group of slice data images that are taken at the same time or the same phase, further uses a plurality of volume data having different times or different phases to draw an image on the monitor. Moreover, this plurality of volume data includes the same site in its range. When 4-dimensional volume analysis processing is executed, the image that is drawn on the monitor 4 is an image that indicates the change over time of a specified site or tissue of the body. In this processing (4-dimensional volume analysis processing), after extracting volume data that comprises a group of slice images taken at the same time or same phase as a combination of medical image data, the CPU 14 further extracts a plurality of volume data of different times or different phases. Change over time may be change over a short period of time such as breathing or pulse, or may be change over a long period of time such as growth of a tumor. As a result, the drawn image may be a 3-dimensional moving image, or maybe an image that expresses the change in movement in a single image (for example, a heart function map that makes it possible to visualize the movement of the heart wall). Also, the image may simply express a numerical value or graph (for example, the speed of growth of a tumor).

CT-PET fusion processing is image processing that uses volume data that comprises slice data images that were taken by a CT device, and volume data that comprises slice data images taken by a PET device to draw a specified site or tissue of the body on the monitor 4. The images drawn by CT-PET fusion processing and specified by a CT device, are images of which the user can easily determine the positional relationship of the surrounding area that includes a specified site or tissue of the body. The images drawn by CT-PET fusion processing and specified by a PET device, are images of which the user can easily determine the affected region or tissue.

Therefore, in this processing (CT-PET fusion processing), mainly a plurality of slice data or volume data that comprises a plurality of slice data that were taken by a CT device, and a plurality of slice data or volume data that comprises a plurality of slice data that were taken by a PET device are extracted by the CPU 14 as a combination of medical image data that conform to CT-PET fusion processing.

Next, MR brain perfusion processing, coronary artery analysis processing and heart function analysis processing will be explained as special image processing.

MR brain perfusion processing is image processing that uses a plurality of slice data that are taken after a contrast agent has been administered by an MRI device as moving images to draw the state of blood flow in the brain by analyzing the process of inflow and outflow of contrast agent by an image that corresponds to parameters that express the state of blood flow (amount of flood flow, amount of blood, average transit time). This plurality of slice data can be used as the routined unit of diagnosis of the image processing.

The routined unit of diagnosis can be a plurality of sites in space, for example, four routined units of diagnosis on four parallel planes. Moreover, the routined unit of diagnosis could be a plurality volume data in a time sequence. Also, the image is a moving image, however, the behavior immediately after the contrast agent is administered is more important, so there is no need for each frame of the moving image to be equally spaced. Furthermore, in this image processing, it is necessary that the data be medical image data in which contrast agent has been administered. The CPU 14 searches for information included in the slice data that uses a contrast agent, and extracts the slice data that use the contrast agent. In perfusion processing, the image processing algorithm differs depending on the imaging device and the target organ, so in addition to MR brain perfusion processing, for example, there is also CT perfusion processing, MRI liver perfusion processing, and the like. Moreover, it is preferred that there be an image of the administered contrast agent with the same coordinates for comparison.

Coronary artery analysis processing is image processing that evaluates the function of the coronary artery by drawing a 3-dimensional medical image of the chest area that includes the contrast marked coronary artery. Therefore, coronary artery analysis processing requires volume data, and furthermore, since the coronary artery comprises very minute tissue, it is necessary that the slice interval be smaller than the preset value (standard value) (or that the image resolution be higher) (this is because a more detailed image is necessary). Moreover, when the user inputs coronary artery processing, the CPU 14 extracts slice data from the chest area having an interval that is less than the standard value and that is slice data that uses a contrast agent based on contrast agent usage information and imaging coordinate information.

Heart function analysis processing is the processing that analyzes whether the heartbeat is normal. Therefore, heart function analysis processing requires a plurality of volume data that correspond to the phase of the heartbeat. The object of observation is the heart chamber, which is a relatively large area, and is surrounded by muscle, so there is no special limit on the slice interval (or image resolution). In many cases, because of the amount of memory, often a combination of slice data having a slice interval (or image resolution) that is larger than in the case of coronary artery analysis processing is used (it is possible to use the same slice data that are used in coronary artery analysis processing and to skip some of the slice data).

As was explained in the explanation above of the image processing and the slice data or volume data that are used in each image processing, there are combinations of slice data or volume data that conform to the type of image processing. Moreover, in this invention, the types of image processing are not limited to those described above.

Furthermore, there are cases in which one type of image processing has conditions for combinations of a plurality of image data (for example, there is fusion processing such as in CT-PET fusion).

It is also possible for one type of image processing to be constructed such that image data is selected (or evaluated) from a plurality of image data. For example, construction is possible in which image data are evaluated from at least slice data that are taken by a CT device or slice data that are taken by a MR device.

Moreover, the CPU 14 is such that it is capable of using the various attribute information (various information such as, patient information, imaging device information, imaging date information, imaging time information, imaging condition information, imaging scale information, and contrast agent usage information) that is included in one of the slice data of the medical image data, and automatically recognizing and extracting the compositional unit of the logical data (can be an address that is physically separated).

In this case, a combination of medical image data is not limited to a unit of files in which medical image data are stored (or saved), or a so-called series of medical images, but is a combination that is created by the CPU 14 having individual images themselves (slice data) as the minimum unit (in the case of calling the data medical image data, this includes a combination of medical image data).

Furthermore, in a CT device, when back-and-forth scanning (images of a specified site or tissue are continuously taken from opposite directions) is performed, each time scanning is performed in one direction, the CPU 14 can recognize and extract the data as a different group of slice data (plurality of slice data).

[7. Explanation of the Flow of the Processing Operation]

Next, the operation of an embodiment of the invention will be explained based on the flowchart shown in FIG. 6.

In step S1, the user uses the keyboard 5 or mouse 6 of the medical image processing device as an input means, and inputs patient information and Study ID information (includes information such as patient information, imaging date of the medical image data and the like) into the medical image processing device to specify the patient.

In step S2, the user uses the keyboard 5 or mouse of the medical image-processing device as an input means, and inputs the type of image processing into the medical image-processing device.

In step S3, based on the patient that was specified by the patient information that was input in step S1 and the type of image processing that was specified by the image processing type that was input in step S2, the CPU 14 extracts combinations of medical image data that conforms to these.

In step S4, the CPU 14 evaluates out combinations of medical image data from the combinations of medical image data that were extracted in step S3 in order of highest possibility of being able to be used for the input image processing.

In step 5, the CPU 14 outputs the evaluating result information, which are the results of the evaluating made in step S4, to the monitor 4, which is an information notification means, and displays the results.

In step S6, the user uses the keyboard 5 or mouse 6 as a selection means, and based on the combination of medical image data, selects from the evaluating result information that was displayed in step S5, to execute the image processing that was input in step 2. Moreover, the medical image-processing device performs computation based on the selected combination of medical image data, and draws (displays) the computational results on the monitor 4 as an image.

Next, FIGS. 7A, 7B will be used to explain an example of the evaluating result information that is displayed on the monitor 4 in step S5.

FIG. 7A is an example of evaluating result information that is displayed on the monitor 4 when the user inputs CT-PET fusion processing as the type of image processing.

In the column on the left side of FIG. 7A, information that indicates which kind of imaging device was used to obtain the medical image data is displayed. In the case of CT-PET fusion processing, images taken by both a CT device and PET device are fused and displayed on the monitor 4, so at the top of the column on the left in FIG. 7A, the text 'CT image' is displayed to indicate that the medical image data ware taken by a CT device, and at the bottom of the column on the left in FIG. 7A, the text 'PET image' is displayed to indicate that the medical image data were taken by a PET device.

In the column in the center of FIG. 7A, combinations of medical image data that can be used in the input image processing are displayed from the top downward in the order of the highest possibility to be requested. In the case of the CT images, it is displayed that the CPU 14 has evaluated out volume data A as having the highest possibility of being used (volume data A is displayed at the very top). In addition, volume data B that is displayed after (below) volume data A is evaluated out by the CPU 14 as having the highest possibility of being used after volume data A.

Also, in the case of the PET images, it is displayed that the CPU 14 has evaluated out volume data C has having the highest possibility of being used (volume data C is displayed at the very top) Moreover, volume data D that is displayed after volume data C is evaluated out by the CPU 14 as having the highest possibility of being used after volume data C.

Furthermore, in the column on the right side of FIG. 7A, numerical values are displayed that indicate the range of the CT images or PET images. The numerical values 100 to 300 for the range displayed in the column for CT images indicate the ID of slice data that make up the volume data (corresponds to the range in the axial direction of the body). These numerical values can be values that are unique to the imaging device used in taking the CT images, or could be values that are based on the coordinate axes that are shared with the imaging device used to take the PET images.

Also, the numerical values from 0 to 50 of the range shown in the column for PET images indicate the ID of slice data that make up the volume data (correspond to the range in the axial direction of the body). Normally, PET images have a lower resolution than CT images. Each of the numerical values is a reference for the user when checking which site or tissue of the body images is to be taken of. In addition, the user is able to select a display range for the images from the displayed range. It is also possible to display slice data images that corresponds to the selected numerical values as a preview.

FIG. 7B is an example of when evaluating result information is displayed on the monitor 4 when the user inputs MRI brain perfusion processing as the image processing.

In the column on the left side of FIG. 7B, information is displayed that indicates which kind of imaging device is used to take images of medical data. In the case of MRI brain perfusion processing, images that are taken by a MRI device are displayed on a monitor 4, SO in the column on the left side of FIG. 7B, the text 'MRI Device' is displayed to indicate that the medical image data are taken by an MRI device.

In the center column of FIG. 7B, a plurality of slice data images (aforementioned routined unit of diagnosis) that were taken as moving images that can be used for the input type of image processing are evaluated and displayed by the CPU 14 in order of coordinates ( moving image data A to moving image data D). In the case of MRI brain perfusion processing, there is a high possibility that all of these routined unit of diagnosis having different coordinates could be used, so it is displayed that the CPU 14 has selected all routined unit of diagnosis having different coordinates.

Moreover, in the column on the right side of FIG. 7B, numerical values are displayed that indicate the range of MRI images. The numerical values for the range from 0 to 45 that are displayed in the column for MRI images indicates the numbers attached to the MRI images in the order that the images were taken. When taking images, the user takes advantage of the timing at which the contrast agent is injected, and is able to select the range from the displayed ranges for displaying a moving image. Normally, there is no particular problem by selecting the entire range.

Next, an example of the algorithm (prediction algorithm (algorithm for selecting the recommended combinations of medical image data)) used in step S4 for setting the priority of combinations of medical image data.

Depending on the type of image processing, the prediction algorithm may be an algorithm for the medical image data that the CPU 14 extracts in step S3.

It is possible to use only one example of the prediction algorithm, or it is possible to use a plurality of prediction algorithms and set a high score for image data when it conforms to a prediction algorithm, and to set the priority of combinations of medical image data higher the higher the total score is.

First, when information that indicates whether or not a combination of medical image data is already being used in image processing is stored as information that is included in the combination of medical image data, the CPU 14 can give priority to and evaluate out combinations of medical image data that are not yet being used in medical image processing.

Moreover, depending on the imaging date information and/or imaging time information of the medical image data, the CPU 14 can evaluate out a combination of the most recent or the oldest medical image data as the combination of medical image data having the highest priority. This is because when there is a plurality of combinations of the same medical image data, the user may want to use the combination of the most recent medical image data in order to know the most recent status of the site of the patient for which the image is taken (when the user, which is a doctor, wants to make a diagnosis immediately after images are taken); on the other hand, the user may want to use the combination of medical image data having the oldest date and time in order to know how the current status of a site of the patient (lesion, etc.) has changed from when images of the site were first taken.

Furthermore, the priority may be set by using the properties of the medical image data. For example, by preferentially evaluating out medical image data having high resolution, it is possible to provide high-quality images (images displayed on the monitor 4) for which image processing was performed using medical image data having the high image quality. Also, when it is only possible to process a small amount of data due to the performance characteristics of the CPU 14 or memory 15, it is possible to set the priority and evaluate out medical image data that matches the performance of the CPU 14 and memory 15. Image processing of medical image data that can be displayed with high resolution may require a long time, so this makes it possible to prevent the occurrence of wasted time.

Moreover, when medical image data are CT images, the CPU 14 finds the distribution of CT values, and it is possible to set the order of priority based on the distribution range of CT values. For example, the range of CT values is set depending on whether the object of image processing is fat, bone, muscle, an organ, etc., so it is possible for the CPU 14 to determine the range of CT values and set the order of priority.

Furthermore, by finding the signal quality (for example, signal to noise ratio S/N) of the medical image data through computation by the CPU 14, it is possible to evaluate out medical image data having the highest quality as the medical image data having the highest priority. In that case, when there is part of the medical image data that has a poor S/N, the CPU 14 is capable of evaluating out that medical image data as medical image data having a low priority. That is because during diagnosis, after taking images over a wide range with a limited amount of irradiation (low S/N ratio), the amount of irradiation is increased and concentrated on areas where lesions are suspect and images are taken (high S/N ratio).

It is also possible to set the order of priority based on the spatial or time sequential relationship between medical image data. For example, it is considered to be possible to provide more detailed information to the user, in case that the spatial interval between medical image data of a combination is smaller. Therefore, it is possible to evaluate out combinations of medical image data having a small spatial interval between medical image data as having high priority. In addition, it is considered to be possible to provide more detailed information (change over time) to the user, when the time sequential (time) interval between medical image data of a combination is shorter. Therefore, it is possible to evaluate out combinations of medical image data having a small time sequential interval between medical image data as having high priority.

It is also possible to set the order of priority based on the direction (location is space) from which the medical image data were taken (the imaging condition information that is included in the medical image data includes information related to the direction from which the medical information was taken (includes information related to the tilt such as non-axial direction information)). For example, in the case of an MRI device, it is possible to take medical image data from any arbitrary direction, however, in the case of a CT device, medical image data is taken from a cross-sectional direction of the body. Moreover, in order to execute image processing for analyzing the heart, in an MRI device, imaging conditions are such that that images are taken of the heart from a specified direction (the imaging condition information contains imaging direction information that indicates from which cross section of the heart images are to be taken instead of the axial direction of the body), so when executing MR heart function analysis processing, which is one kind of image processing, the CPU 14 recognizes the imaging condition information, so it is possible to preferentially evaluate out medical image data that was taken from a cross section of the heart by an MRI device (or it is possible to extract the medical image data as extraction data in step S3).

Furthermore, it is possible for the CPU 14 to set the order of priority of medical image data based on the operation history of the user. Information regarding the type of image processing, the extraction conditions for medical image data, and selection results by the user are included in the operation history of a user.

For example, when medical image data are selected that meet the specified condition of just the type of image processing set by the user, information indicating that medical image data that meet the specified condition was selected for the specified image processing is stored in the operation history information of the user. Therefore, when the specified type of image processing is input, the CPU 14 preferentially extracts and evaluates out medical image data that meet the preferentially specified condition. This happens in the case of selecting medical image data having a specified resolution. Also, for example, when a combination of medical image data is selected according to the specified condition of just the type of image processing that is specified by the user, information indicating that a combination of medical image data was selected according to specified conditions for the specified image processing is stored in the operation history information of the user. Therefore, when a specified type of image processing is input, the CPU 14 preferentially extracts and evaluates out combinations of medical image data that meet the preferentially specified condition. This happens in the case when selecting a combination of medical image data within a specified range.

Moreover, it is possible to set the order of priority of medical image data by storing information for all examination data (including medical image data) that has been input for a patient in a memory device such as a database 2, and then having the CPU 14 check that examination data.

Furthermore, it is possible to set the order of priority of medical image data by storing learning history information related to the learning history of medical image data that is used in image processing in a memory device such as a database 2, and having the CPU 14 check that learning history information For example, when a combination of medical image data that was preferentially evaluated out for image processing in the past is not selected by the user, based on the learning history information that medial image data was preferentially evaluated out but not selected by the user, the CPU 14 can improve the operability of the image processing device for the user by not preferentially evaluating out that medical image data when the same image processing is input.

Also, it is possible to improve the operability of the image-processing device by the user by having the CPU 14 reference the learning history information of certain medical image data, and by executing medical image data similar to that medical image data with the same priority as that medical image data.

An image-processing device executes an embodiment of the present invention based on FIG. 6, however, there are variations, and they will be explained below.
<Variation 1>

Figure 6:
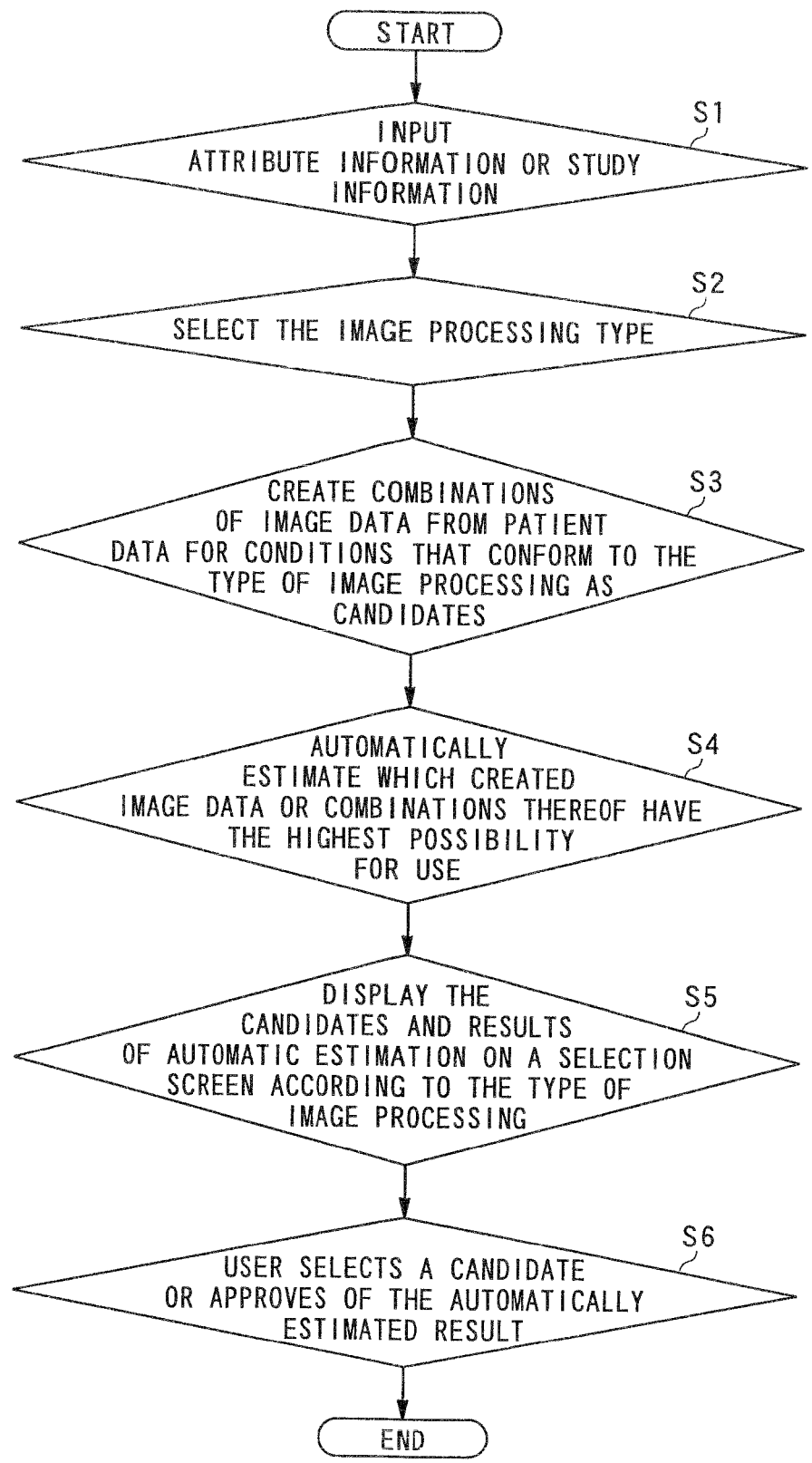
FIG. 6 is a flowchart showing an example of the Raycast method used in an embodiment of the invention.

After the CPU 14 executes step S4 in FIG. 6, the CPU 14 can download medical image data that is determined in step S4 to have the highest priority from the database 2 to the main memory 15 beforehand without waiting for the user to select medical image data in step S6.

After the CPU 14 has preferentially extracted and evaluated medical image data in step S4, time might be required before the user selects a combination of medical image data in step S6. Therefore, in that case, by downloading a combination of medical image data having high priority to the main memory 15 with high execution speed beforehand, the time required for downloading the medical image data (time for reading medical image data) appears to be reduced, so the response speed of the image processing device is improved, and it becomes possible to improve operability of the image processing device by the user.

In step S6, when the user does not select medical image data that were preferentially evaluated out by the CPU 14, the CPU 14 does not use the data that were read to the main memory 15 in advance, but newly reads the medical image data that were selected in step 6 from the database 2 to the main memory 15.
<Variation 2>

When the user selects medical image data in step 6 as shown in FIG. 6 and the image processing device executes the image processing that was input in step S2, in the case where settings for drawing an image are preset for the medical image data currently being executed, the CPU 14 draws an image with those set image drawing settings for the medical image data that is read to the main memory 15.

For example, by executing various pre-processings for medical image data that were taken the previous time a patient was in the hospital before executing the image processing from the previous time again, it becomes possible for the user to select a combination of medical image data for which pre-processing has been executed by having the CPU 14 execute the same pre-processing for the medical image data that were taken this time.

Moreover, when a spatial range is selected as a special range for the combination of medical image data in FIG. 7A, the CPU 14 prepares the same range in the main memory 15 as medical image data to be used next.

Also, when a process for skipping data is performed in advance for the combination of medical image data currently being executed before executing image processing, then next, for the same image processing, the CPU 14 performs the process for skipping data on the combination of medical image data that were predicted to be executed next (for example, the combination of medical image data that is next in the order of priority) and prepares the main memory 15 for the medical image data to be used next.

When the medical image data currently being executed forms volume data, and the conditions for the volume data are set (for example, when the range of CT values is preset, when the opacity value is preset, when the color values are preset, when the gradient shading is preset, etc.), the CPU 14 performs the processing according to the drawing conditions that are set for volume data on the combination of medical image data that is predicted to be executed in the next image processing (for example, the combination of medical image data that is next in the order of priority), and prepares those data in the main memory 15 as the combination of medical image data to be used next.

When conditions that are preset for a combination of medical image data for which image processing is being performed is known in this way, the CPU 14 performs the preset conditions for the combination of medical image data to be used next, and prepares that combination of medical image data on which condition processing has been executed in the main memory 15.

Therefore, since a combination of medical image data, for which processing has been performed to set suitable processing conditions, is prepared for the next image processing after the image processing currently being executed, it becomes easy for the user to confidently select that combination of medical image data as the medical image data to be executed next.

Moreover, when the user routinely (when the work that is performed according to a preset procedure, and the combination of medical image data to be used next is clearly known) and orderly proceeds in performing diagnosis work, by performing the processing described above beforehand, the CPU 14 can more efficiently execute image processing, and thus a user-friendly image processing device can be constructed whose operation is not complicated for the user, and that does not cause the user to feel stress.

Furthermore, when the user orderly performs the work of comparing images of the same site that are displayed on the monitor 4, or when the user observes a plurality of medical image data in succession for a single patient, by performing the processing described above beforehand, a user-friendly image processing device can be constructed whose operation is not complicated for the user, and does not cause the user to feel stress.

<Variation 3>

When the user selects a combination of medical image data in step S6 as shown in FIG. 6, and the image processing device executes the image processing that was input in step S2, and when there is empty space in the main memory 15 other than that being used for image processing, the CPU 14 can further read in advance other medical image data from the database 2 that conforms to the type of image processing that was input in step S2.

For example, the CPU 14 can read a combination of medical image data into the main memory 15 beforehand that are medical image data that were taken previously for the patient that was input in step S1, and that was processed by the same type of image processing that is currently being performed.

The CPU 14 can also read into the main memory 15 beforehand medical image data for which the pre-processing of variation 2 was executed.

In this case as well, a user-friendly image processing device can be constructed whose operation is not complicated for the user, and that does not cause the user to feel stress.

<Variation 4>

In the case of executing the image processing that was input in step S2, it is possible for the CPU 14 to set desired conditions between volume data for the input image processing.

For example, in the case where CT-PET fusion is input as the image processing, medical image data from a CT device and medical image data from a PET device of the same site of a body are used. In this case, the user normally performs the work of selecting medical image data that was taken on the same date as the medical image data from the CT device and medical image data from the PET device.

Therefore, when CT-PET fusion is the input as the type of image processing, by having the CPU 14 extract and evaluate out combinations of medical image data from a CT device and medical image data from a PET device that were taken on the same date so that the user can make a selection, it is possible to construct a user-friendly image processing device whose operation is not complicated for the user, and that does not cause the user to feel stress.

Moreover, in the case where CT-PET fusion is the input as the type of image processing, by having the CPU 14 extract and evaluate out combinations of medical image data from a CT device and medical image data from a PET device that were taken of the same site (including surrounding tissue) so that the user can make a selection, it is possible to construct a user-friendly image processing device whose operation is not complicated for the user, and that does not cause the user to feel stress.

Furthermore, when image processing is the input that handles moving images such as in the case of 4-dimension volume analysis processing or heart function analysis processing, it is possible to set the same conditions that were set for the first medical image data in a time sequence (conditions such as the range, or whether or not there is filtered processing) and execute the same processing for medical image data that follows in the time sequence. In this case, when the first medical image data is volume data, the same processing as was performed for the first volume data is performed for the volume data that follows, and it is possible to provide that data to the user for selection. Therefore, it is possible to construct a user-friendly image processing device whose operation is not complicated for the user, and that does not cause the user to feel stress.

<Variation 5>

After the image process that was input in step S2 has been executed based on the combination of medical image data that was selected in step S6, it is possible to change patients and perform the same image processing.

For example, in the case of a medical facility that concentrates on performing heart function examination and coronary artery examination, there may be cases in which it is desired to perform heart function analysis processing continuously one after the other. In this type of situation, the condition (slice interval used for calculation) for the combination of medical image data when heart function analysis processing is performed for a patient A is standardized by that medical facility. Moreover, heart function analysis processing for the next patient B is performed for the combination of medical image data for patient B, and the condition for that combination is the same as the condition for the combination of medical image data for patient A. At this time, by using that condition to extract the combination of medical image data to be used in heart function analysis processing, it is possible to efficiently extract medical image data for heart function examination from among the medical image data that were obtained in the heart function examination and coronary artery examination.

<Other Variations>

As was described above, the present invention includes various embodiments, however, in addition to the embodiments (or variations) described above, it is also possible to construct the present invention as described below.

Volume data can be such that image processing can be executed using only part (spatially or according to time) of the volume data, so it becomes possible to automatically predict beforehand that part of the volume data.

Moreover, in the conditions (specifications) that are suitable to the image processing, a series of moving images (moving image data) or volume data can logically be taken to be the unit of the combinations of medical image data. These logical combinations of medical image data may also include one item of slice data. Also, when a logical combination of medical image data comprises a plurality of medical image data, the storage location of the logical medical image data in memory can be various locations (can be in separate memory devices, or can be various addresses in one memory device), or can be collected and stored in one continuous storage area.

Furthermore, it is possible to predict and/or automatically set the conditions for drawing the volume data (conditions for drawing the image such as whether or not to use interpolation, whether or not to perform filter processing, selection of a color map, selection of an opacity LUT (Look Up Table), image angle, magnification rate when drawing the image, etc.).

In the embodiments described above, information that was set by an imaging device as attribute information for the medical image data was used, however, the attribute information could also be set by using parameters that are found by analyzing the image information of the medical image data. For example, the CPU 14 can find the distribution of CT values, and based on the distribution range of the CT values, can determine the kind of tissue that is included in the image.

For example, whether the object of image processing is fat, bone, muscle, and organ or the like is determined according to the range of CT values, so it is possible to determine an organ that is desired as the object of image processing, and to use that to extract a combination of medical image data.

Furthermore, by storing the combinations of medical image data described above in a memory device as file information, it is possible next time to use medical image data having the same conditions as a file.

It is also possible to store medical image data on a server and to make the image processing device function as a client-server type system.

By storing the operating procedure shown in FIG. 6 beforehand on a recording medium such as a hard disc, or storing it beforehand by way of a network such as the Internet, and then reading and executing that operating procedure by a general-purpose microcomputer or the like, it is possible to make that general-purpose microcomputer function as the CPU of the embodiments of this invention.

With this invention, combinations of medical image data, which are suitable candidates that conform to the image processing desired by the user, can be presented to the user from among an enormous amount of medical image data.

Moreover, the user can select a suitable combination of medical image data that conforms to the desired image processing, so it is possible to prevent the user from selecting the wrong combination of medical image data, and the selection operation by the user itself is simplified.

Furthermore, in the case where the user must observe a plurality of medical image data (series) for the same patient one after the other, redundant operation by the user has been done away with, so it is possible for the user to perform the selection operation quickly and easily.

Furthermore, construction is such that combinations of medical image data that are candidates having the highest priority are presented to the user, so when a presented combination of medical image data coincides with the selection of combination of medical image data by the user, operation by the user is simplified by increasing the speed of image processing and doing away with operation related to explicit selection.

Furthermore, the image processing device automatically performs the extraction and evaluating (arranging the order of priority) of combinations of medical image data, so for a user that must process a large amount of images for medical use in a single day, it is possible to do away with the complicated operation of extracting and evaluating combinations of medical image data, and thus it is possible to lighten the burden on the user and to greatly reduce judgmental and operational errors.

Furthermore, when performing image processing using a combination of medical image data that was selected by the user, drawing settings are performed that correspond to the method used for visualizing the medical image data that is recommended for the respective types of image processing, so it is possible to eliminate the time required for the user to reset the drawing settings, and since uniform and standardized drawing can be performed, more accurate analysis can be expected.

Furthermore, the image-processing device can provide the user with volume data that comprises a plurality of slice data in a 3-dimensional array as a combination of medical image data. Therefore, the image-processing device can create a set of image data for routined unit of diagnosis having with a high degree of freedom and having few restraints on the logical format, and thus is able to provide medical image data or a combination of medical image data in routined diagnosis easy for the user to handle.

Furthermore, the routined unit of diagnosis of the medical image data is a unit that fits the senses of the user, so display screens are easy to view and it becomes possible to perform suitable judgment for image processing. Furthermore, it is possible to lighten the burden on the user and to greatly reduce judgmental and operational errors.

Furthermore, when the input image processing type is fusion processing, it is known in advance that the image processing is image processing that uses at least two or more combinations of medical image data for the region around the same site, so by searching for medical image data for the same site, the work of searching for medical image data that is suitable for image processing from among an enormous amount of medical image data is simplified.

Furthermore, the amount of operation by the user is reduced, and the design becomes user friendly.

Furthermore, various information is included in the medical image data, so when the user executes the desired image processing, the image processing device is able to quickly extract combinations of medical image data that conform to the image processing desired by the user from a large amount of medical image data.

Furthermore, since there is no repeated burden on the user to frequently operate the user interface to search for medical image data, it is possible to provide the user with an image-processing device having good operability.

Furthermore, construction is such that combinations of medical image data that are best candidates having the highest priority are provided to the user, so when evaluating by the image processing device (prioritizing combinations of medical image data) coincides with the selection of a combination of medical image data by the user, it is possible to speed up the image processing.

Furthermore, the image processing device automatically extracts and evaluates (prioritizes) combinations of medical image data, and without waiting to obtain medical image data having a slow transfer speed, stores combinations of medical image data having high priority onto a high-speed memory medium inside the image processing device before the user performs any operation, so a high-speed image processing device that can immediately execute image processing with little wait time by the user is possible.

Furthermore, there may be cases in which there are combinations of medical image data for each imaging period when observing the progression over time of a certain patient for example. In that case, observation is performed using combinations of medical image data that include the most recent progression over time, and when for comparison it is desired to observe past progression over time using the similar form, by processing suitable combinations of medical image data that include past progressions over time, it is possible to perform the objective examination more quickly.

Furthermore, there may be cases, such as in a screening examination, where the same examination is performed in succession for different patients. In that case, it is convenient to perform image processing in succession using the same conditions for the different patients. With this invention, the user is presented with combinations of medical image data having the same conditions, so it is possible to perform examination more quickly and with objectivity.

Furthermore, when the image processing device stores combinations of medical image data that were selected before by the user as log information, and the same image processing is input by the user, the image processing device searches for combinations of medical image data based on that log information (learning function), so a faster and more efficient image processing device becomes possible.

With this invention, the image processing device can be used as a client server type image processing device instead of as a stand-alone type of device, so by storing medical image data in an external database, the medical image database can be easily maintained, and it becomes possible for many users to use (share) medical image data from a terminal device.

This invention is not limited to the above embodiments or examples, but may be appropriately changed without departing from the spirit or scope of the invention as read from the claims and the description. Such modified display units may also fall within the technical scope of the invention.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

The entire disclosure of Japanese Patent Application No. 2007-301947 filed on Nov. 21, 2007 including the specification, claims, drawings and summary is incorporated herein by reference in its entirety.

What is claimed is:

1. A medical image processing device that uses medical image data that contains attribute information comprising:
   an input means for inputting medical information that includes at least patient information, and an image processing type that uses the medical image data;
   an extraction means for using at least the attribute information to extract combinations of the medical image data that conform to the patient information and the image processing type;
   an evaluating means for evaluating combinations of medical image data from the combinations of medical image data extracted by the extraction means that have the highest possibility of being used in image processing of the image processing type;
   an information reporting means for reporting of the combinations of medical image data and evaluating result information, which is the result of evaluation by the evaluating means; and
   a selection means for prompting a user to select the combination of medical image data that was reported by the information reporting means.

2. The medical image-processing device of claim 1, wherein there are drawing settings that correspond to the type of image processing; and after the selection means selects the combination of medical image data, the medical image data are drawn according to the drawing settings.

3. The medical image-processing device of claim 1, wherein the combinations of medical image data form at least volume data.

4. The medical image-processing device of claim 1, wherein when the image processing type is fusion processing information, the extraction means extracts at least two combinations of medical image data of the region around the same site of the patient.

5. The medical image-processing device of claim 1, wherein the patient information is included in the attribute information of the medical image data, and furthermore, at least one or more of imaging device information, imaging date information, imaging time information, imaging condition information, imaging coordinate information, imaging scale information, and information of whether or not a contrast agent is used are included as attribute information.

6. The medical image processing device of claim 1, further comprising an acquisition means for acquiring beforehand the combinations of medical image data that were evaluated out by the evaluating means before a user uses the selection means to select the combination of medical image data.

7. The medical image-processing device of claim 1, wherein conditions that were used when the extraction means extracted the combination of medical image data that was selected by the selection means and the patient information, are used in extracting a new combination of medical image data that conforms to the type of image processing.

8. The medical image-processing device of claim 1, wherein conditions that were previously used when the extraction means extracted the combination of medical image data that was selected by the selection means and the patient information of an another patient of the patient of the patient information is stored, are used in extracting a new combination of medical image data that conforms to the type of image processing.

9. The medical image-processing device of claim 1, wherein the extraction means uses the combination of medical image data that was selected in the past by the selection means based on an image processing type, which is the same as the image processing type that was input by the input means, to extract a new combination of medical image data.

10. The medical image-processing device of claim 1, wherein the medical image data are acquired from a medical image data storage means.

11. A method for controlling a medical image processing device that uses medical image data that contains attribute information, comprising:
   an input process of inputting medical information that includes at least patient information, and an image processing type that uses the medical image data;
   an extraction process of using at least the attribute information to extract combinations of the medical image data that conform to the patient information and the image processing type;
   a evaluating process of evaluating out combinations of medical image data from the combinations of medical image data extracted in the extraction process that have the highest possibility of being used in image processing of the image processing type;
   an information reporting process of reporting of the combinations of medical image data and evaluating result information, which is the result of evaluating in the evaluating process; and
   a selection process of prompting a user to select the combination of medical image data that was reported in the information reporting process.

12. The method of controlling a medical image-processing device of claim 11, wherein there are drawing settings that correspond to the type of image processing; and after the selection means selects the combination of medical image data, the medical image data are drawn according to the drawing settings.

13. The method of controlling a medical image-processing device of claim 11, wherein the combinations of medical image data form at least volume data.

14. The method of controlling a medical image-processing device of claim 11, wherein when the image processing type is fusion processing information, at least two combinations of medical image data of the region around the same site of the patient are extracted in the extraction process.

15. The method of controlling a medical image-processing device of claim 11, wherein the patient information is included in the attribute information of the medical image data, and furthermore, at least one or more of imaging device information, imaging date information imaging time information, imaging condition information, imaging coordinate information, imaging scale information, and information of whether or not a contrast agent is used are included as attribute information.

16. The method of controlling a medical image processing device of claim 11, further comprising an acquisition process of acquiring beforehand the combinations of medical image data that were evaluated out in the evaluating process before a user selects the combination of medical image data in the selection process.

17. The method of controlling a medical image-processing device of claim 11, wherein conditions that were used in the extraction process when extracting the combination of medical image data that was selected by the selection means and the patient information, are used in extracting a new combination of medical image data that conform to the type of image processing.

18. The method of controlling a medical image-processing device of claim 11, wherein conditions that were used in the extraction process when extracting the combination of medical image data that was selected by the selection means and patient information of an another patient of the patient of the patient information is stored, are used in extracting a new combination of medical image data that conforms to the type of image processing.

19. The method of controlling a medical image-processing device of claim 11, wherein the extraction process uses the combination of medical image data that was selected in the past in the selection process based on an image processing type, which is the same as the image processing type that was input in the input process, to extract a new combination of medical image data.

20. The method of controlling a medical image-processing device of claim 11, wherein the medical image data are acquired from a medical image data storage process.

21. A non-transitory computer-readable medium encoded with a control program for a medical image-processing device that causes a computer having a processor that is included in the medical image-processing device, which uses medical image data that contains attribute information, to function as:
   an input means for inputting medical information that includes at least patient information, and an image processing type that uses the medical image data;
   an extraction means for using at least the attribute information to extract combinations of the medical image data that conform to the patient information and the image processing type;
   an evaluating means for evaluating out combinations of medical image data from the combinations of medical image data extracted by the extraction means that have the highest possibility of being used in image processing of the image processing type;
   an information reporting means for reporting of the combinations of medical image data and evaluating result information, which is the result of evaluating by the evaluating means; and
   a selection means for prompting a user to select the combination of medical image data that was reported by the information reporting means.

22. The control program for a medical image-processing device of claim 21, wherein there are drawing settings that correspond to the type of image processing; and after the selection means selects the combination of medical image data, the medical image data are drawn according to the drawing settings.

23. The control program for a medical image-processing device of claim 21, wherein the combinations of medical image data form at least volume data.

24. The control program for a medical image-processing device of claim 21, wherein when the image processing type is fusion processing information, the extraction means extracts at least two combinations of medical image data of the region around the same site of the patient.

25. The control program for a medical image-processing device of claim 21, wherein the patient information is included in the attribute information of the medical image data, and furthermore, at least one or more of imaging device information, imaging date information, imaging time information, imaging condition information, imaging coordinate information, imaging scale information, and information of whether or not a contrast agent is used are included as attribute information.

26. The control program for a medical image processing device of claim 21, further comprising n acquisition means for acquiring beforehand the combinations of medical image data that were evaluated out by the evaluating means before a user uses the selection means to select the combination of medical image data.

27. The control program for a medical image-processing device of claim 21, wherein conditions that were used when the extraction means extracted the combination of medical image data that was selected by the selection means and the patient information, are used in extracting a new combination of medical image data that conforms to the type of image processing.

28. The control program for a medical image-processing device of claim 21, wherein conditions that were used when the extraction means extracted the combination of medical image data that was selected by the selection means and patient information of an another patient of the patient of the patient information is stored, are used in extracting a new combination of medical image data that conforms to the type of image processing.

29. The control program for a medical image-processing device of claim 21, wherein the extraction means uses the combination of medical image data that was selected in the past by the selection means based on an image processing type, which is the same as the image processing type that was input by the input means, to extract a new combination of medical image data.

30. The control program for a medical image-processing device of claim 21, wherein the medical image data are acquired from a medical image data storage means.

* * * * *